(12) United States Patent
Masuda

(10) Patent No.: US 9,221,847 B2
(45) Date of Patent: Dec. 29, 2015

(54) IONIC LIQUID

(71) Applicant: Nisshinbo Holdings Inc., Tokyo (JP)

(72) Inventor: Gen Masuda, Chiba (JP)

(73) Assignee: NISSHINBO HOLDINGS INC., Tokyo (JP)

( * ) Notice: Subject to any disclaimer, the term of this patent is extended or adjusted under 35 U.S.C. 154(b) by 0 days.

(21) Appl. No.: 14/435,897

(22) PCT Filed: Oct. 7, 2013

(86) PCT No.: PCT/JP2013/077212
§ 371 (c)(1),
(2) Date: Apr. 15, 2015

(87) PCT Pub. No.: WO2014/061482
PCT Pub. Date: Apr. 24, 2014

(65) Prior Publication Data
US 2015/0266906 A1    Sep. 24, 2015

(30) Foreign Application Priority Data

Oct. 16, 2012  (JP) ................................. 2012-229067

(51) Int. Cl.
C07F 7/08    (2006.01)
C07D 207/06  (2006.01)

(52) U.S. Cl.
CPC ............ C07F 7/0818 (2013.01); C07D 207/06 (2013.01)

(58) Field of Classification Search
None
See application file for complete search history.

(56) References Cited

U.S. PATENT DOCUMENTS

| 3,141,898 | A | 7/1964 | Tiers |
| 6,900,257 | B2 | 5/2005 | Chowdhury et al. |
| 2004/0094741 | A1 | 5/2004 | Sato et al. |

FOREIGN PATENT DOCUMENTS

| JP | 2005-535690 A | 11/2005 |
| JP | 2007-161733 A | 6/2007 |
| WO | 2009/020038 A1 | 2/2009 |
| WO | 2013/005712 A1 | 1/2013 |

OTHER PUBLICATIONS

International Search Report dated Dec. 17, 2013, issued in corresponding application No. PCT/JP2013/077212.
CMC Publishing, "Ionic Liquids : The Front and Future of Material Development", Feb. 1, 2003, (28 pages).
CMC Publishing, "Ionic Liquid II—Marvelous Developments and Colorful Near Future-", Mar. 30, 2006, (20 pages).

*Primary Examiner* — Michael Barker
(74) *Attorney, Agent, or Firm* — Westerman, Hattori, Daniels & Adrian, LLP

(57) ABSTRACT

Provided is an ionic liquid comprising a cyclic quaternary ammonium cation indicated by formula (1) and a trimethylsilyl alkanesulfonate anion indicated by formula (2).

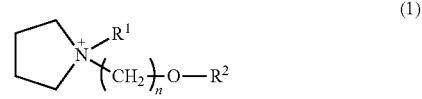

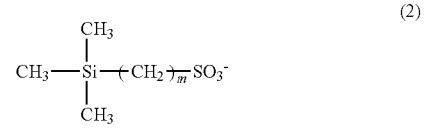

(In the formula, $R^1$ indicates a C1-3 alkyl group, $R^2$ indicates a methyl group or an ethyl group, n indicates 1 or 2, and m indicates 2 or 3.)

10 Claims, 2 Drawing Sheets

IONIC LIQUID

TECHNICAL FIELD

The present invention relates to an ionic liquid.

BACKGROUND ART

The term "ionic liquid" refers to a salt composed solely of ions which generally has a melting point of 100° C. or below. Ionic liquids have attracted attention because of their outstanding characteristics such as non-volatility, flame retardance and high ionic conductivity, and also because their properties and functions can be variously designed. On account of such qualities, ionic liquids are regarded as promising for such applications as solvents in green chemistry that is gentle on the environment, and as electrolytes in electrical storage devices.

However, because most hitherto known ionic liquids include halogen atoms such as fluorine atoms on the anion, there remain problems with these from the standpoint of their environmental impact. Moreover, halogen-free ionic liquids are known to be inferior to ordinary fluorine-containing anion-containing ionic liquids in terms of their physical properties; for example, they have a poor heat resistance and a high viscosity.

In order for ionic liquids to be used in electrochemical applications such as electrolytes for electrical storage devices, they are required to have electrochemical properties such as a high ionic conductivity and a wide potential window. Such ionic liquids have hitherto been reported, although these have halogen atoms, and especially fluorine atoms, on the molecule. Ionic liquids which are halogen-free and also have a wide potential window have not hitherto been known.

CITATION LIST

Patent Document

Patent Document 1: JP-A 2005-535690

SUMMARY OF INVENTION

Technical Problem

It is therefore an object of the present invention to provide an ionic liquid which does not contain halogen atoms, has an excellent heat stability as a halogen-free ionic liquid, and has a wide potential window compared with conventional ionic liquids.

Solution to Problem

The inventor, as a result of extensive investigations aimed at achieving the above object, has discovered that salts which are composed of a specific cyclic quaternary ammonium cation having an alkoxyalkyl group and a trimethylsilyl alkanesulfonate anion form ionic liquids, and moreover have an excellent heat resistance as halogen-free ionic liquids. The inventor has also found that such ionic liquids have a broad potential window compared with conventional ionic liquids.

Accordingly, the invention provides:
1. An ionic liquid characterized by including a cyclic quaternary ammonium cation of formula (1) below and a trimethylsilyl alkanesulfonate anion of formula (2) below

[Chemical Fomula 1]

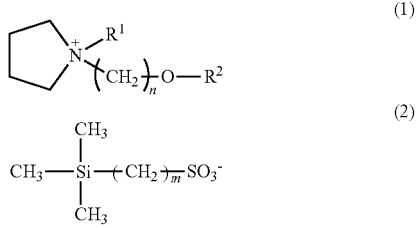

wherein $R^1$ is an alkyl group of 1 to 3 carbons, $R^2$ is a methyl group or an ethyl group, n is 1 or 2, and m is 2 or 3.
2. The ionic liquid of 1 above, wherein $R^1$ is a methyl group or an ethyl group.
3. The ionic liquid of 2 above, wherein $R^1$ and $R^2$ are both methyl groups.
4. The ionic liquid of any one of 1 to 3 above, wherein n is 2.
5. The ionic liquid of any one of 1 to 4 above, wherein m is 3.

Salts composed of a trialkylsilyl alkanesulfonate anion and a quaternary onium cation have been disclosed in, for example, Patent Document 1. However, these salts are not the ionic liquid of the invention.

Advantageous Effects of Invention

The ionic liquids of the invention are halogen-free and thus have little environmental impact. Moreover, they have an excellent heat resistance compared with conventional halogen-free ionic liquids, and also have a wide potential window compared with conventional ionic liquids and are thus electrochemically stable.

BRIEF DESCRIPTION OF THE DIAGRAMS

DESCRIPTION OF EMBODIMENTS

Figure 1:
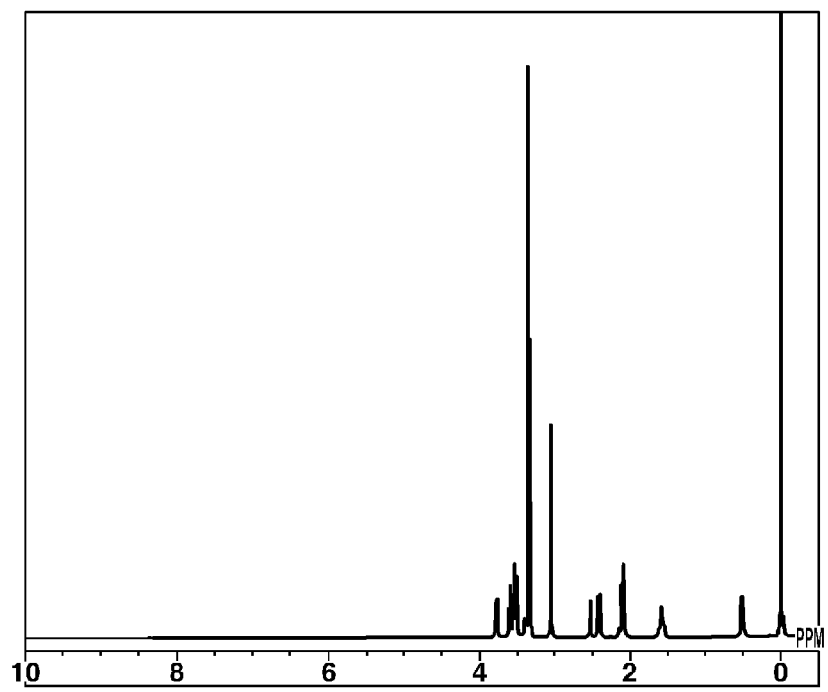
FIG. 1 is an $^1$H-NMR spectrum of Compound 1 obtained in Example 1.

The ionic liquid of the invention is composed of a cyclic quaternary ammonium cation of formula (1) below and a trimethylsilyl alkanesulfonate anion of formula (2) below.

[Chemical Formula 2]

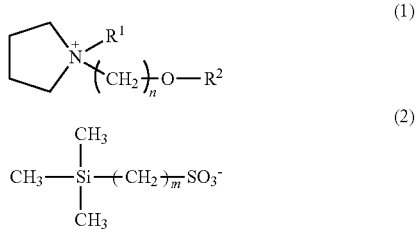

In the above formulas, $R^1$ is an alkyl group of 1 to 3 carbons, and $R^2$ is a methyl group or an ethyl group. The letter "n" is 1 or 2, although 2 is especially preferred from the standpoint of chemical stability. The letter "m" is 2 or 3, although 3 is especially preferred from the standpoint of ready availability of the starting materials.

The alkyl group may be linear, branched or cyclic, and is exemplified by methyl, ethyl, n-propyl, i-propyl and c-propyl. Of these, a linear alkyl group is preferred, with methyl or ethyl being more preferred.

The cyclic quaternary ammonium cation of above formula (1) is most preferably one in which both $R^1$ and $R^2$ are methyl groups.

The melting point of the ionic liquid of the invention is preferably 100° C. or less, more preferably 80° C. or less, and even more preferably 50° C. or less.

The ionic liquid of the invention may be prepared by, for example, using a cyclic quaternary ammonium salt of formula (3) below and a trimethylsilyl alkanesulfonate salt of formula (4) below and carrying out ion exchange using an ion-exchange resin.

[Chemical Formula 3]

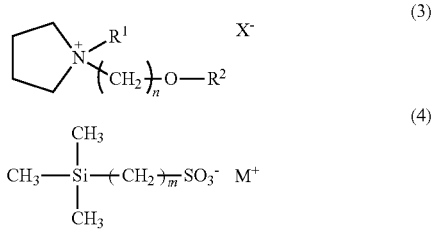

In these formulas, $R^1$, $R^2$, n and m are as defined above, X is a halogen atom, and $M^+$ is a monovalent metal ion.

Specifically, first an aqueous solution of the quaternary ammonium salt of formula (3) is passed through a column filled with a cation-exchange resin, causing the cations of the quaternary ammonium salt to be supported on the cation-exchange resin, and the column is rinsed by passing water through. Next, the trimethylsilyl alkanesulfonate salt of formula (4) is passed through the column and the eluate is recovered and purified, thereby giving the target ionic liquid.

The cation-exchange resin used here may be a commonly used cation-exchange resin, although the use of a strongly acidic cation-exchange resin is preferred. Such cation-exchange resins may be procured as commercial products.

The cyclic quaternary ammonium salt of formula (3) may be synthesized by a common known method for synthesizing amines. For example, it may be synthesized by reacting pyrrolidine with an alkoxyalkyl halide to give a tertiary amine, then reacting the tertiary amine with an alkylating agent.

The trimethylsilyl alkanesulfonate salt of formula (4) may be synthesized using a known method (e.g., the method described in U.S. Pat. No. 3,141,898). Alternatively, the sulfonate salt for which m=3 in formula (4) may be procured as a commercial product.

The halogen atom represented by X above is exemplified by fluorine, chlorine, bromine and iodine, with chlorine, bromine and iodine atoms being preferred.

The metal ion represented by $M^+$ is exemplified by sodium, potassium and silver ions. From the standpoint of cost, a sodium ion or a potassium ion is preferred.

Aside from the above method of synthesis, the ionic liquid of the invention may also be synthesized by common methods of synthesis described in publications (e.g., *Ion-sei ekitai—Kaihatsu no saizensen to mirai* [Ionic liquids: Latest developments and future prospects], CMC Publishing, 2003; *Ion ekitai II—Kyouiteki na shinpo to tasai na kinmirai* [Ionic liquids II: Amazing advances and near-term promises], CMC Publishing, 2006). For example, production may be carried out by reacting the cyclic quaternary ammonium salt of formula (3) with the sulfonate salt of formula (4) in a solvent. In this case, the solvent may be either water or an organic solvent.

The relative proportions in which the cyclic quaternary ammonium salt and the trimethylsilyl alkanesulfonate salt are used in the reaction may be set to a molar ratio of from about 5:1 to about 1:5. Carrying out the reaction at a molar ratio close to 1:1 is generally preferred.

Following reaction completion, the product can be obtained by carrying out an ordinary work-up.

Another exemplary method of preparing the ionic liquid of the invention is a neutralization method that uses an ion-exchange resin. In the case of this neutralization method, first a trimethylsilyl alkanesulfonate salt and a cyclic quaternary ammonium salt are converted into a trimethylsilyl alkanesulfonic acid and a cyclic quaternary ammonium hydroxide using, respectively, a cation-exchange resin and an anion-exchange resin, following which the two are mixed together to give the ionic liquid.

When this neutralization method is employed in the invention, so long as ion exchanges are carried out on both the trimethylsilyl alkanesulfonate salt and the cyclic quaternary ammonium salt, the counterions are not subject to any particular limitations. However, from the standpoint of cost, sodium salts, potassium salts and the like are preferred as the trimethylsilyl alkanesulfonate salts. The counterion for the cyclic quaternary ammonium salt is preferably a halide ion, with a chloride ion or a bromide ion being especially preferred from the standpoint of cost.

The molar ratio between the trimethylsilyl alkanesulfonic acid and the cyclic quaternary ammonium hydroxide in the above neutralization reaction is not particularly limited, and may be set to from about 5:1 to about 1:5. Taking cost into consideration, it is preferable to carry out the reaction at a molar ratio close to 1:1. It is especially preferable to have the neutralization point of the aqueous phase to be the reaction endpoint.

The ionic liquid of the invention described above is useful as a reaction solvent and as an extraction solvent. Because it is a halogen-free ionic liquid, it is particularly useful as a green solvent having a low environmental impact.

It can also be used as an electrolyte (a liquid electrolyte) for electrical storage devices, or as an antistatic agent or plasticizer for addition to polymeric materials such as rubbers and plastics. Because the ionic liquid of the invention has an excellent heat resistance compared with other halogen-free ionic liquids, it is highly suitable for such applications. In particular, because the ionic liquid of the invention has a wide potential window compared not only with conventional ionic liquids, but even with conventional solid electrolyte salts, and is thus electrochemically stable, it can most advantageously be used as, for example, an electrolyte (a liquid electrolyte) in electrical storage devices.

EXAMPLES

Working Examples of the invention and Comparative Examples are given below by way of illustration, although the invention is not limited by the following Examples.

The analytical instruments and conditions used in the Examples were as follows.

[1] $^1$H-NMR Spectrum
  Instrument: AL-400, from JEOL Ltd.
  Solvent: Deuterated DMSO

[2] Melting Point
  Instrument: DSC 6200, from Seiko Instruments, Inc.
  Measurement conditions:
    Measured by raising the temperature 10° C./min from 20° C. to 60° C., holding the temperature at 60° C. for 1 minute, then lowering the temperature 1° C./min from 60° C. to −90°, holding the temperature at −90° C. for 1 minute, then raising the temperature 1° C./min from −90° C. to 60° C.

[3] Decomposition Point
  Instrument: TG-DTA 6200, from Seiko Instruments, Inc.
  Measurement conditions:
    Measured in an air atmosphere while raising the temperature 10° C./min from 30° C. to 500° C. The temperature at which the weight decreased 10% was treated as the decomposition point.

[4] Cyclic Voltammetry Measurement
  Instrument: HSV-100 Electrochemical Measurement System, from Hokuto Denko Corporation
  Measurement conditions:
    Using a glassy carbon electrode as the working electrode, a platinum electrode as the counterelectrode, and a Ag/Ag$^+$ reference electrode, measurement was carried out at a sweep rate of 10 mV/sec.

Example 1

Synthesis of Compound (1)

Compound 1 of the following formula was synthesized.

[Chemical Formula 4]

Compound 1

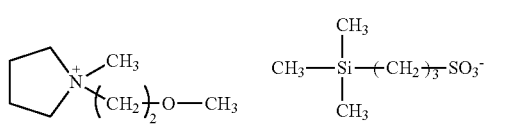

Pyrrolidine (Wako Pure Chemical Industries, Ltd.), 1.51 parts by weight, and 2-methoxyethyl chloride (Kanto Chemical Co., Inc.), 1.00 part by weight, were mixed together and reacted for 1 hour under refluxing. Following the reaction, the reaction mixture was separated into two phases, then left to cool for a while, whereupon the bottom phase solidified. The top phase alone was collected by decantation, and purification was carried out by vacuum distillation. This distillation gave 0.96 part by weight of the target substance N-2-methoxyethylpyrrolidine (boiling point, 76° C.; vapor pressure, 45 mmHg) in a yield of 70%.

Next, 1.00 part by weight of the resulting N-2-methoxyethylpyrrolidine was mixed with a two-fold volume of toluene (Wako Pure Chemical Industries, Ltd.), the mixture was placed in an autoclave and the interior of the system was flushed with nitrogen. The system was closed, then about 1.00 part by weight of methyl chloride gas (Nittoku Kagaku Kogyo KK) was added under stirring at room temperature. During introduction of the methyl chloride gas, the temperature and internal pressure both rose; at the highest point, the temperature rose to about 53° C. and the internal pressure rose to 5.5 kgf/cm$^2$. The reaction was effected in this way without heating; after 2 days, about 0.75 part by weight of methyl chloride gas was added. The reaction was additionally continued for one day, after which the pressure was released. The crystals that had formed within the system were separated off by vacuum filtration and then dried using a vacuum pump, thereby giving 1.29 parts by weight of N-2-methoxyethyl-N-methylpyrrolidinium chloride (yield, 92%).

The cation-exchange resin Amberlist 15JS-HG.DRY (Organo Corporation) was packed into an approximately 20 mL column and exchanged to the hydrogen form. An aqueous solution of 55 g of N-2-methoxyethyl-N-methylpyrrolidinium chloride (MEMPCl) dissolved in 100 mL of deionized water was passed through the packed column, after which deionized water was thoroughly passed through the column until the eluate reached neutrality. After carrying out this and similar operations a plurality of times, the eluate obtained when N-2-methoxyethyl-N-methylpyrrolidinium chloride had been passed through was confirmed to be substantially neutral, indicating that the resin had been converted to the N-2-methoxyethyl-N-methylpyrrodinium form. Following such conversion, deionized water was thoroughly passed through the column and the eluate was confirmed to be neutral. An aqueous solution of 7.57 g of sodium 3-(trimethylsilyl)-1-propanesulfonate (from Sigma-Aldrich Co.) dissolved in 150 mL of deionized water was then passed through the column. The eluate was recovered, then concentrated by reducing the pressure using a vacuum pump and removing the water by distillation. A vacuum was then pulled for 1.5 hours while heating the distillation residue to 110° C. on an oil bath, thereby giving 11.3 g of the target substance: Compound 1 (yield, 95%).

The $^1$H-NMR spectrum of Compound 1 thus obtained is shown in FIG. 1.

Compound 1 had a melting point of 40° C. and a decomposition point of 293° C.

Example 2

Synthesis of Compound 2

Compound 2 of the following formula was synthesized.

[Chemical Formula 5]

Compound 2

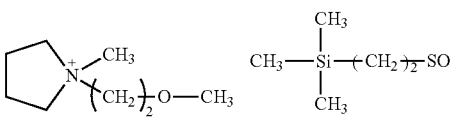

Aside from using sodium 2-(trimethylsilyl)-1-ethanesulfonate instead of sodium 3-(trimethylsilyl)-1-propanesulfonate, Compound 2 was synthesized as a liquid by the same method as in Example 1. The sodium 2-(trimethylsilyl)-1-ethanesulfonate was synthesized according to the method described in U.S. Pat. No. 3,141,898.

Figure 2:
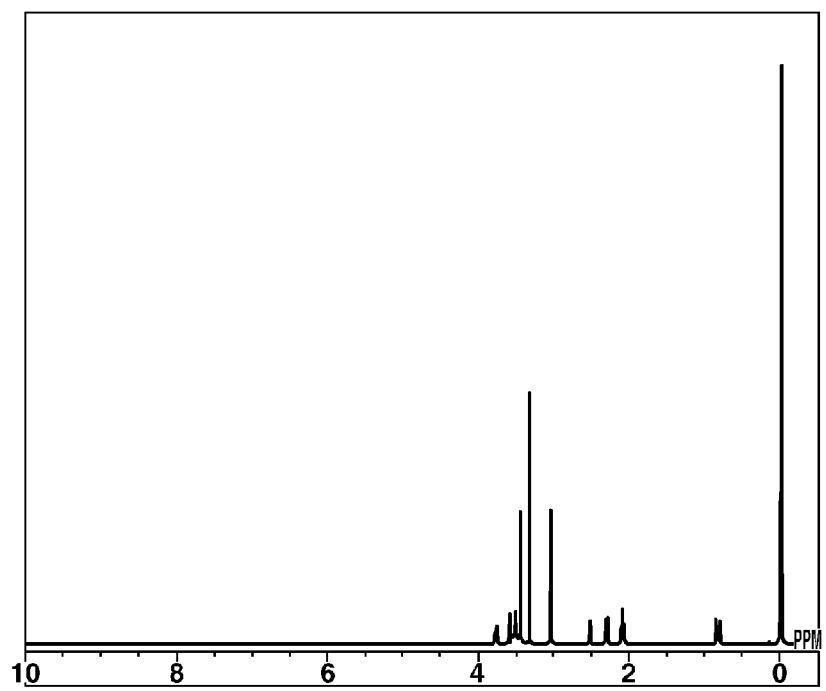
FIG. 2 is an $^1$H-NMR spectrum of Compound 2 obtained in Example 2.

The $^1$H-NMR spectrum of the resulting Compound 2 is shown in FIG. 2.

A melting point was not observed for Compound 2. The glass transition point was −70° C. and the decomposition point was 285° C.

Comparative Example 1

Synthesis of Compound 3

Compound 3 of the following formula was synthesized according to the method described in JP-A 2007-161733. Compound 3 had a melting point of 18° C., and a decomposition point of 360° C.

[Chemical Formula 6]

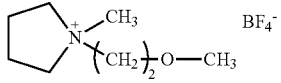

Compound 3

[Cyclic Voltammetry Measurements]

0.1 M Propylene carbonate (Kishida Chemical Co., Ltd.) solutions were prepared of each of above Compounds 1 to 3, and cyclic voltammetry measurement was carried out.

Figure 3:
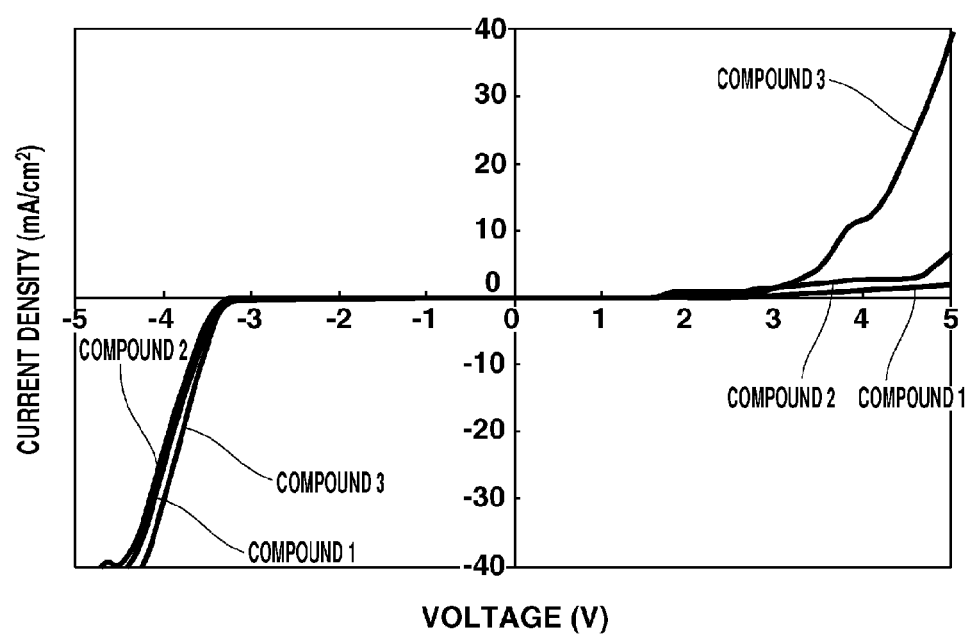
FIG. 3 is a chart showing the potential windows of above Compounds 1 and 2 and of Compound 3 obtained in Comparative Example 1.

The results are shown in FIG. 3. As is apparent from FIG. 3, Compounds 1 and 2 have broad potential windows, from which it was apparent that they are electrochemically stable.

The invention claimed is:

1. An ionic liquid characterized by comprising a cyclic quaternary ammonium cation of formula (1) below and a trimethylsilyl alkanesulfonate anion of formula (2) below

[Chemical Formula 1]

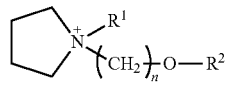
(1)

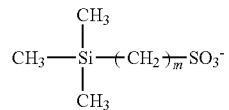
(2)

wherein $R^1$ is an alkyl group of 1 to 3 carbons, $R^2$ is a methyl group or an ethyl group, n is 1 or 2, and m is 2 or 3.

2. The ionic liquid of claim 1, wherein $R^1$ is a methyl group or an ethyl group.

3. The ionic liquid of claim 2, wherein $R^1$ and $R^2$ are both methyl groups.

4. The ionic liquid of claim 1, wherein n is 2.

5. The ionic liquid of claim 1, wherein m is 3.

6. The ionic liquid of claim 2, wherein n is 2.

7. The ionic liquid of claim 3, wherein n is 2.

8. The ionic liquid of claim 2, wherein m is 3.

9. The ionic liquid of claim 3, wherein m is 3.

10. The ionic liquid of claim 4, wherein m is 3.

* * * * *